United States Patent [19]
Kashuba et al.

[11] Patent Number: 5,908,423
[45] Date of Patent: Jun. 1, 1999

[54] FLEXIBLE MEDULLARY REAMING SYSTEM

[75] Inventors: Glen A. Kashuba, Union City; Antony Koblish, Montclair; Jay Bichet, Aberdeen, all of N.J.

[73] Assignee: Howmedica, Inc., New York, N.Y.

[21] Appl. No.: 08/557,159

[22] PCT Filed: May 10, 1994

[86] PCT No.: PCT/IB94/00103

§ 371 Date: Mar. 4, 1996

§ 102(e) Date: Mar. 4, 1996

[87] PCT Pub. No.: WO94/27507

PCT Pub. Date: Dec. 8, 1994

Related U.S. Application Data

[63] Continuation-in-part of application No. 08/068,488, May 27, 1993, abandoned.

[51] Int. Cl.⁶ .................................................. A61B 19/00
[52] U.S. Cl. .............................................. 606/80; 408/127
[58] Field of Search ...................... 606/167, 170, 606/79, 80, 81; 408/127, 199, 224, 225, 226, 227

[56] References Cited

U.S. PATENT DOCUMENTS

| | | |
|---|---|---|
| 1,725,299 | 8/1929 | Pickin . |
| 2,786,218 | 3/1957 | Yousem . |
| 3,554,192 | 1/1971 | Isberner . |
| 3,838,937 | 10/1974 | Hawley . |
| 4,706,659 | 11/1987 | Matthews et al. . |
| 4,738,256 | 4/1988 | Freeman et al. . |
| 4,751,922 | 6/1988 | DiPietropolo . |
| 4,790,852 | 12/1988 | Noiles . |
| 5,098,436 | 3/1992 | Ferrante et al. . |
| 5,122,134 | 6/1992 | Borzone et al. . |

FOREIGN PATENT DOCUMENTS

| | | |
|---|---|---|
| 441 601 | 8/1991 | European Pat. Off. . |
| 496 636 | 7/1992 | European Pat. Off. . |
| 502 738 | 9/1992 | European Pat. Off. . |
| 2542056 | 3/1977 | Germany . |
| WO 92/10138 | 6/1992 | WIPO . |

*Primary Examiner*—William Lewis
*Attorney, Agent, or Firm*—Pennie & Edmonds LLP

[57] ABSTRACT

An apparatus for reaming a bone canal, such as the medullary canal of a femur, has a flexible shaft (12, 92) with a proximal end (16) for engaging a rotary transmission source. A first reamer (14, 61) is coupled to the distal end of the flexible shaft for rotation therewith to prepare the distal portion of the canal. A second reamer (22, 93) coupled with the proximal portion of the shaft to form the proximal end of the lateral portion of the canal and/or the medial calcar region of the canal. The apparatus further comprises a metaphyseal template (70, 80) having the shape of the prosthesis for guiding the reaming apparatus in forming the calcar region of the canal.

31 Claims, 9 Drawing Sheets

FLEXIBLE MEDULLARY REAMING SYSTEM

CROSS-REFERENCE TO RELATED APPLICATIONS

The present application, national stage of International Application No. PCT/IB94/00103, is a Continuation-in-Part of U.S. application Ser. No. 08/068,488, filed May 27, 1995, now abandoned.

BACKGROUND OF THE INVENTION

1. Field of the Invention

This invention relates to a technique and instruments for performing orthopedic surgeries such as total hip arthroplasty. This technique allows a long bone, such as a femur, to be prepared to receive a prosthesis, such as a total hip replacement, by reaming a lateral bore, in the bone, until the isthmus using a series of reamers on a flexible shaft and then reaming the calcar region of the bone. The invention specifically relates to a combination of specially shaped remers that match the prosthesis shape and a flexible shaft that provides control, and allows the reamers to be angled in a controlled manner to shape the bone canal to fit the prosthesis line-to-line.

2. Description of the Prior Art

Surgeons strive for accurate, replicable surgical techniques so that precise fits can be obtained between the prosthesis and bone. It is believed that in a non-cemented application a precise fit enhances prosthesis life. This increased contact area between bone and prosthesis has been shown to improve long-term fixation. Accurate bone preparation for cemented prostheses will also provide improved long-term fixation due to precise and optimal cement mantle thickness between bone and the prosthesis.

There has been a growing movement in the orthopedics community to move away from bone preparation that involves introducing large impact forces from hammer blows. Current surgical bone preparation technique involves shaping the bone by introducing a broach or rasp type device with a hammer. This can result in large dynamic stresses within the bone, which has been known to crack or deform the bone in some cases. Even with this drawback, broaching is widely used because it allows for very irregular, non-symmetric shapes for non-symmetric prostheses to be formed in bone. The broach is shaped exactly like the prosthesis with an appropriate gap or undersize condition for interference fit accounted for and impacted into a bone cavity that has been initially opened with straight or tapered reamers.

The traditional or current approach to forming the bone envelope for total joint replacement is generally termed a three step process, excluding the ostectomy, with multiple iterations per step. First a series of distal reamers are passed into the isthmus, swing up on each pass until cortical contact is felt. Next, a series of tapered mid-shaft or conical reamers are introduced in incremental sizes to shape the mid-shaft portion of the bone and to remove proximal lateral bone and to notch the greater trochanter to ensure neural alignment. Lastly, a series of incrementally sized broaches are impacted into the bone to remove proximal medial bone and to clean up any remaining bone from the lateral and distal areas. Leaving so much bone behind for the broaches to remove results in much hammering and impact stresses in the bone. So much so, that some surgeons have been known to do a prophylactic cerclage of the proximal bone with either wire or a clamp to prevent cracking while impacting the broach. The instruments required for this technique include two or three distal reamers, two tapered mid-shaft reamers, two broaches—broach handles/impactor extractors and hammers and an optional prophylactic cerclage device.

Commercially available jigs for off-axis reaming are not able to ream curves, rather than angles, around corners nor are they able to control the sizing and alignment of the medullary canal.

SUMMARY OF THE INVENTION

The technique and instruments of the present invention offer the advantage that the bone cavity can be formed completely by reaming. No impact forces are introduced to the femur by broaching or rasping. The number and types of instruments has been reduced and the number of steps to prepare the femur are also reduced. The technique of the present invention with new instruments reduces femoral preparation to a two step process. Instruments that are eliminated from the traditional technique include broaches, broach handles/impactors/extractors, hammers and the need for prophylactic cerclage. The now technique involves dividing the femoral canal into three areas (one—distal/isthmus, two—mid-shaft/proximal lateral, three—proximal medial). Each section is prepared with its own specially reamer. The shaping sequence first includes distal reaming to cortical contact, which is similar to the traditional procedure. Next, reaming the mid-shaft and proximal late and notching the greater trochanter over a flexible shaft attached to distal spacer. This will also seat the spacer and able shaft. The medial reamer, which is tapered to fit the medial flare of the prosthesis exactly, is moved at an angle by flexing the shaft via a bail and socket on the flexible shaft. The flexible shaft provides the necessary control to ream while articulating the medial reamer through a 15° arc.

The flexible shaft can either be metal wound or polymeric and provides the unique combination of versatility for condensing steps and control to ream at multiple angles depending on prosthesis size and/or the section being reamed in each individual bone. The surgeon controls the amount of flex induced in the centralized shaft and, consequently, how much bone he removes with each flex or pass. All bone is also cleared from the inside along the neutral axis thereby allowing for all the subtle curves of the bone canal to be shaped without scalloping or flattening them by passing straight or tapered reamers from the outside through a fixed jig. All hip prostheses are curved, especially medially. Thus, the technique of the present invention preserves and enhances the curves of the medullary canal to accommodate the hip prosthesis.

However, it has been further found that advantages may be obtained by using a reaming apparatus, as described above, in conjunction with a metaphyseal template which may be considered a "hollow" version of the prosthesis. At a position spaced from the proximal and distal ends thereof, the template is shaped the same as a strip from the prosthesis' proximal edge. The distal section of the template, depending on the type of reaming apparatus used, may be terminated at the end of the calcar region of the bone or may be a cannulated cylinder corresponding to the distal portion of the lateral bore 52 that is machined to the same distal diameter as the implant. The rest of the template is hollow allowing it to be seated within the lateral bore. The flexible metaphyseal reamer is then introduced into the template (hollow sections) and manipulated around the proximal (implant shaped) template. The flexible action of the reamer allows the remaining bone to be shaped to match the curves of the prosthesis (medially & anteriorly-posteriorly).

The combined use of the metaphyseal template and metaphyseal flexible reamer allows for the femoral canal to be formed primarily by reaming. Large, dynamic, impact forces delivered to the bone during conventional broaching are effectively reduced or eliminated. Minimal impact intramedullary canal preparation (reaming) reduces the possibility of cracks and deformation.

The metaphyseal template also provides the added capability of serving as a sizing device. Intraperatively, after the distal canal is sized and/or reamed to cortical, the template is introduced axially into the lateral bore of the bone (see FIG. 7) and the outline of the prosthesis (proximally), after setting the anteversion, is seated into the osteotomy cut. This allows you to check proximal fit medially & anterior-posterior prior to final canal preparation. This added information, allows for final proximal fit to be judged without introducing progressively larger broaches/rasps until the proper size (tight fit) is achieved. Use of broaches or rasps, for sizing, requires extensive experience and judgment in cementless implants. There is a fine line between tight proximal fit and exceeding the ultimate strength of the bone when it is subjected to a wedge-like hoop-stress (resulting in cracks).

Another added benefit of the metaphyseal template is its ability to be used as an alignment guide. The long, axial shape of the template allows for the most proximal section to be used as a sight to indicate neutral position in the medial-lateral plane. This is possible due to the distal cylinder matching the diameter of the last reamer passed in the isthmus. This line-to-line distal fit assures that the template will seat itself in the same manner as the implant. The template may also be used to set the proper amount of anteversion as well. The axis may be rotated to move the proximal outline of the implant into the proper version. When this is set, the outline can be fixed in the proper position by tapping it into the proximal osteotomy.

The combination of the metaphyseal template and the metaphyseal flexible reamer provides a safe non-impact based method of bone canal preparation. Reaming asymmetric off-axis curved shapes in a controlled manner is now possible. This technique also ensures exact match between proximal and distal machining (even though they are performed independently).

The curvature of the medullary canal, as formed according to the invention, rather than the angles formed according to the prior art, allows the implant shape to more closely match the curvature of the anatomy.

Other advantages of the reamer-template combination include requiring only a reamer of one size for an entire range of implant sizes; cutting texture on proximal/lateral side of template to enhance bone removal in that zone and provides the ability to get better (more stable) fixation when seated. The tapered bushing on the proximal flexible reamer allows the reamer to ride more smoothly on the template. The bushing is also a safety device in that he reamer moves more laterally as the depth of the medullary canal increases and, does not violate (impinge) the medial profile. The short reamer section is also designed for safety as it tends to segment the medial curved profile rather than reaming flat spots.

Thus, it is an object of the invention to provide a set of surgical instruments which allows for the preparation of a bone canal utilizing reaming steps only.

It is a further object of the invention to provide a set of instruments for preparation of a bone canal which allows for the precise preparation of the canal so that a prosthesis corresponding in size and shape to the reamers may be implanted therein.

It is yet another object of the invention to provide a method for preparing a bone canal which is quicker to perform by the surgeon and which imparts less stress to the bone.

These and related objects are achieved in the present invention by an apparatus for reaming a bone canal which includes means for forming a lateral bore in, and removing the bone material from the calcar region of, a bone.

In a first embodiment the apparatus comprises a flexible shaft having a first end, for engagement with a rotary power transmission source, a second end fixedly coupled to a first reaming element for rotation therewith and a second reaming element having a bore therethrough, for slidably receiving the flexible shaft, and a distal end which, when slid onto the flexible shaft is adjacent the first reaming element.

In one aspect of the above embodiment, the apparatus comprises a third reaming element having a bore therethrough for slidably receiving the flexible shaft which also has an end for engaging a second end of the second reaming element. A ball and socket arrangement is formed on the respective first end of the third reamer and the second end of the second reamer to permit universal movement of the second and third reamers. The second and third rears include coupling elements so that they may be driven either directly or indirectly by the rotary power transmission source. The cutting surface of the third reaming element may be cylindrical or concave.

Preferably, to second reamer has a generally conical shape tapering radially inwardly from the second end thereof to its first end. The third reamer has a concave cutting surface for cutting a convex shape in the bone surrounding the canal. This is accomplished by flexing the flexible shaft with the third reamer in place, and rotating. For accurately locating the first and second reamers, the flexible shaft may have a stop element attached thereto or formed as part of the first reamer, which may be fixed to the shaft to contact and locate the first end of the second reamer with respect to the axial length of the shaft.

The reamers are so designed that at the junction of at least two of the reamers, a ball and socket type joint is provided to permit universal movement between the two reamers so that when the shaft is flexed from the proximal end thereof, the proximal third reamer may be displaced from the longitudinal axis of the bone to thereby cut the convex shape in, for example, the calcar area of a femur. If such a convex shape is not desired, the third reamer could, of course, have a cylindrical shape. Either helical or straight grooves may be formed on the reamers of the present invention and rake angles produce smooth cutting of cortical bone may be provided, which rake angles are usually positive and generally about 7°.

These and other object and advantages of the present invention will become apparent from the following description of the accompanying drawings, which disclose several embodiments of the invention. It is to be understood that the drawings are to be used for the purposes of illustration only, and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENTS

Referring to FIGS. 1 through 4, there is shown a first embodiment of a reaming apparatus of the present invention generally denoted as 10. The reaming apparatus includes a flexible reamer shaft 12 which may be either spiral wound metallic material or a composite material. A suitable composite shaft is disclosed in U.S. Pat. No. 4,751,992, which issued on Jun. 21, 1988. Another suitable flexible shaft is described in U.S. Pat. No. 3,554,192, which issued on Jan. 12, 1971. Spiral wound flexible shafts are well known in the art.

Flexible reamer shaft 12 includes a distal head 14 fixedly attached to the distal end thereof for rotation therewith and a rigid proximal end 16 for connection to a rotatory driving source (not shown). Distal head 14 has a distal cutting head or reamer 18 of any well known design and a stop flange 20. Stop flange 20 is provided with a pair of pins 21 and 23 extending generally parallel to shaft 12.

Figure 1:
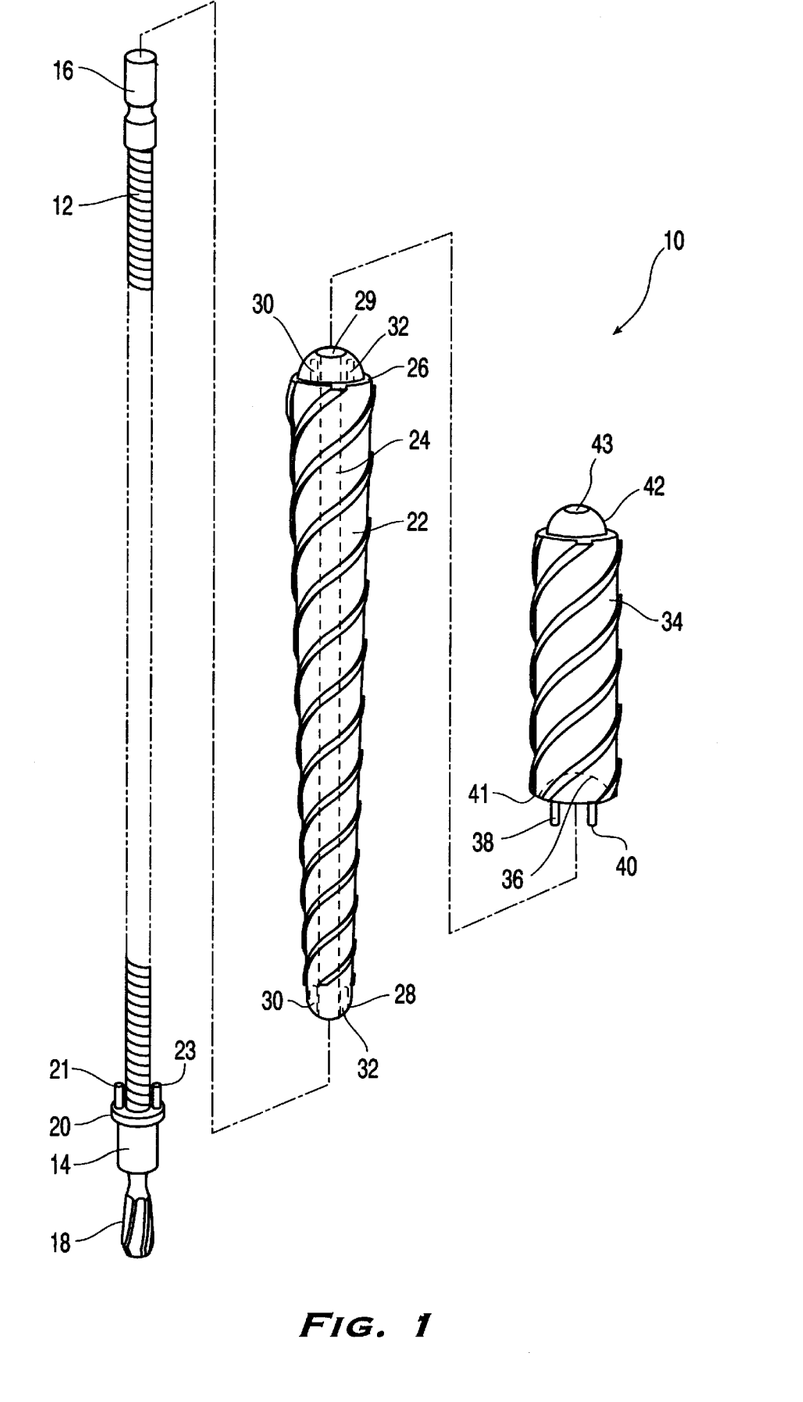
FIG. 1 is an exploded view of the reaming apparatus of the present invention, including three reamers.
Figure 2:
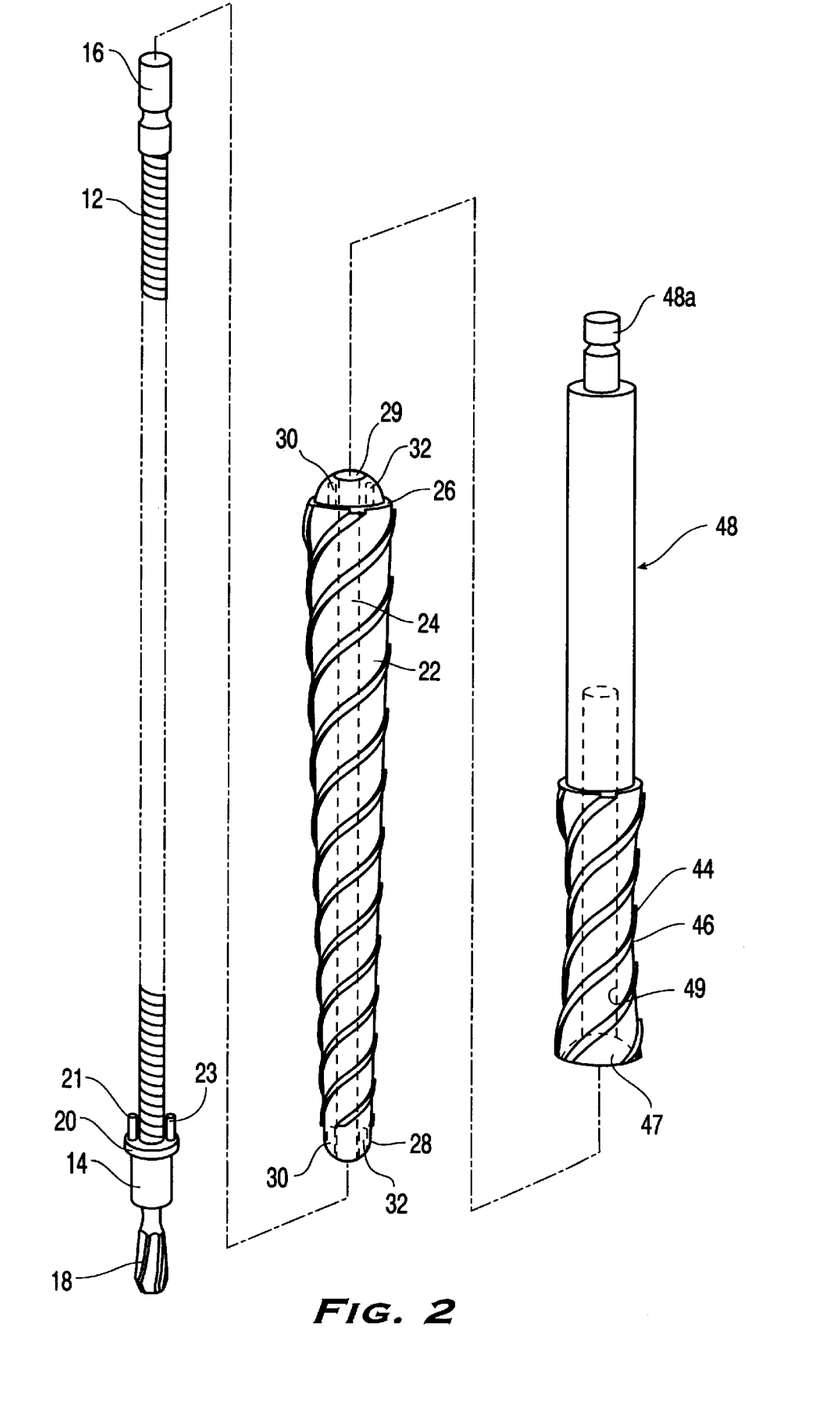
FIG. 2 is an exploded view similar to FIG. 1 with the exception that the third reamer has a concave shape and may be independently driven by a power source.
Figures 3, 4:
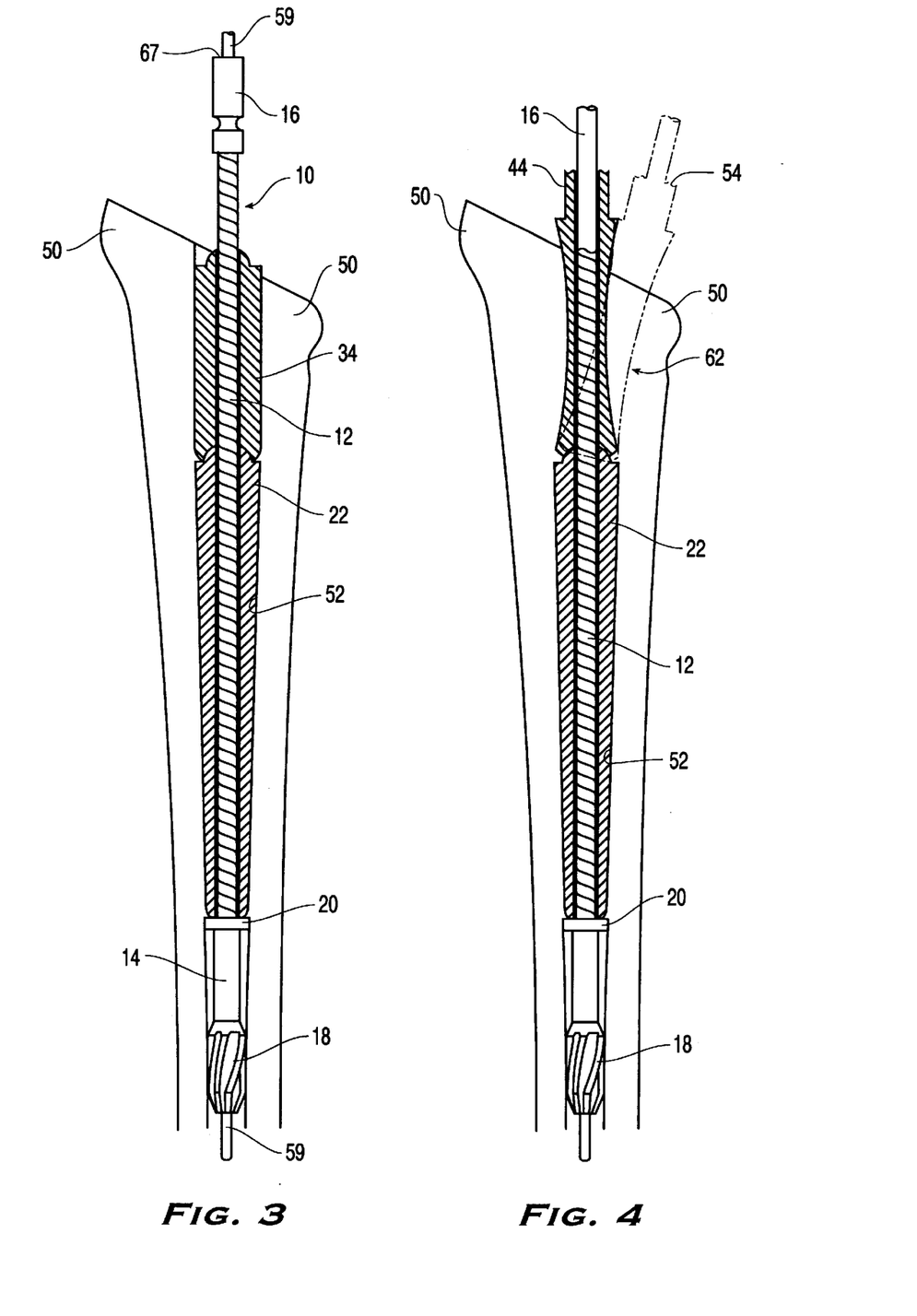
FIG. 3 is an elevation view, partially in cross-section, of a modification of the reaming apparatus of FIG. 1 situated inside a long bone.
FIG. 4 is an elevation view, partially in cross-section, similar to FIGS. 2 and 3, wherein a third reamer having a concave shape has been placed on the second reamer for rotation thereon, as shown in phantom.

A reamer 22 having a bore 24 and sized to slide over shaft 12 into position as shown in FIGS. 3 and 4. As shown in FIGS. 1 and 2 reamer 22 tapers from a first end 26 thereof to its tip 28. A first pair of holes 30 and 32 is formed in a hemispherical surface 29 located at first end 26 and a second pair of holes 30 and 32 is located at tip 28. The function of these holes will be described hereinafter.

A third reamer 34 includes a hemispherical cavity forming a socket 36 at its distal end for receiving the hemispherical surface 29 of retainer 22. The distal end of reamer 34 further comprises a pair of pins 38 and 40 which extends distally for insertion into proximal holes 30 and 32, respectively, of reamer 22. Pins 38 and 40 serve to transfer rotary motion from reamer 22 to reamer 34. Reamer 34 includes a hemispherical surface 42 so that, if necessary, an additional reamer having a socket similar to 36 may be placed thereon.

Referring to FIG. 2 there is shown an exploded view of the reaming system of FIG. 1, wherein third reamer 34, which has a cylindrical shape, has been replaced by a reamer 44 having a concave cutting surface 46. Reamer 44 includes a hollow cavity 49 for receiving the proximal and of flexible shaft 12 so that reamer 44 may be independently driven via drive connection 48. Thus, reamer 44 may be rotated, on surface 29 of reamer 22 by coupling a power source to end 48 while shaft 12 remains non-rotating.

FIGS. 3 and 4 show reaming system 10 inserted in a long bone 50 such as a femur. FIG. 3 shows reamer 34 positioned proximally of reamer 22. Flange 20 acts to locate ream 34 and 22 with rasped to reamer 18. After the lateral bore 52 is formed by reaming with the system 10 of FIG. 1, reamer 34 is removed and reamer 44 placed over the flexible shaft so that it may be independently driven and flexed along with the shaft into the position shown in phantom and labeled 54 in FIG. 4. This allows reaming an arc in the calcar area 62 of the resected long bone 50.

The surgical procedure of the present invention includes initially reaming the lateral bone canal 52 with reamer 18. A guide wire 59, as shown in FIG. 3, may be used to initially locate and guide reamer 18 and shaft 12 within the canal. The use of a guide wire 59 requires that the shaft 12 and reamer 18 be cannulated in a well known manner. The bone is prepared for reaming by penetrating the superior cortex at the trochanteric fossa by known means such as a starter drill or box chisel. If a guide wire 59, as shown in FIG. 3, is used a bore to receive same is also formed in the lateral portion of the bone, until the isthmus, by known means. The guide wire may be positioned in long bone 50 prior to insertion of the shaft 12 and reamer 18 to form canal 52. Reamer 22 is then slid over the flexible shaft 12 as shown in FIG. 3. Reamer 22 shapes the distal area of the bone with a shape matching that of an implant or prosthesis which implant is to be permanently placed within the canal 52 by a "press fit". Reamer 34 is then placed onto reamer 22 to ream the proximal lateral portion of the bone canal again to a shape matching the proximal implant shape in the lateral area. Reamers 22 and 34 are driven via a drive coupling formed by holes 30 and 32 in reamer 22 and pins 21 and 23, 38 and 40 on reamers 18 and 34 respectively. After the lateral bone canal 52 has been formed reamer 34 is replaced by reamer 44. Flexible shaft 12 may then be flexed as show in FIG. 4 to ream the calcar area 62 using reamer 44. This shape matches the concave shape of the typical prosthesis to be implanted (not shown). A trial prosthesis may be used to check the canal shape.

Reamer 44 can be driven off of drive shaft 12, as reamers 22 and 34 were, but, in a preferred embodiment, reamer 44 is driven independently of shaft 12 and is, therefore, provided with a solid shaft 48 at its second end the shaft 48 comprising a connect 48a, at its proximal end, for connection to a rotary power transmission source. Cavity 49 is provided in reamer 44 so that the second end of shaft 12, including solid portion 16, may be received and located therein to permit reamer 44 to rotate about shaft 12 when being independently driven by means of connector 48, at its second end, which is connected to a rotary power transmission source (not shown) through connector 48a.

After reamer 44 has shaped the calcar region 62 of the bone, shaft 12, along with reamers 18, 22 and 44, is removed from the now fully prepared lateral bore 52. The implant may now be press fit into the correctly shaped canal.

Figure 5:
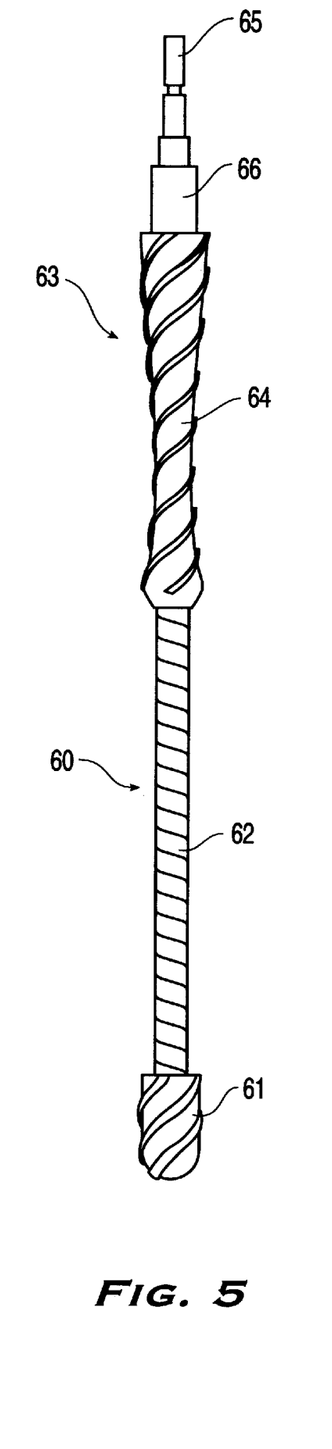
FIG. 5 is an elevational view of a second embodiment of the flexible reaming apparatus of the present invention.

A second embodiment of the reaming system of the present invention, generally denoted as 60, is shown in FIG. 5. In this embodiment a flexible shaft 62 has a first head 61 fixedly attached to its first end and a reamer 63 fixedly to its second end. The second end of reamer 63 is attached to the first end of a solid shaft 66 having a connector 65 at its second end for connection to a rotary power transmission source (not shown). Reamer 63 has a concave cutting surface 64 similar to surface 46 of reamer 44. When used to ream the calcar region 62 of the bone connector 65 would be so situated that the concave cutting surface 64 will be adjacent to the proximal portion of the calcar area of the bone.

Head 61, comprising a smooth outer surface, serves to locate and centralize reamer system 60 and act as a bearing to reduce the torque required to drive reamer 63 when forming the calcar region. In addition, while in the preferred embodiment head 61 and reamer 63 are fixed to shaft 62, reamer 63 could be made so that it could be easily removed.

The use of the reamer system 60 allows for the preparation of the medullary canal in fewer steps and with more accuracy than with previous reaming systems. Head 61 is inserted into the distal canal to the point where concave surface 64 is at the proper location in the lateral bone. Reamer 63 is then moved towards the calcar region by flexing flexible shaft 62. The surgeon continues moving reamer 63 into contact with bone until a correct fit for the prosthesis is obtained.

Figures 6A, 6B, 7:
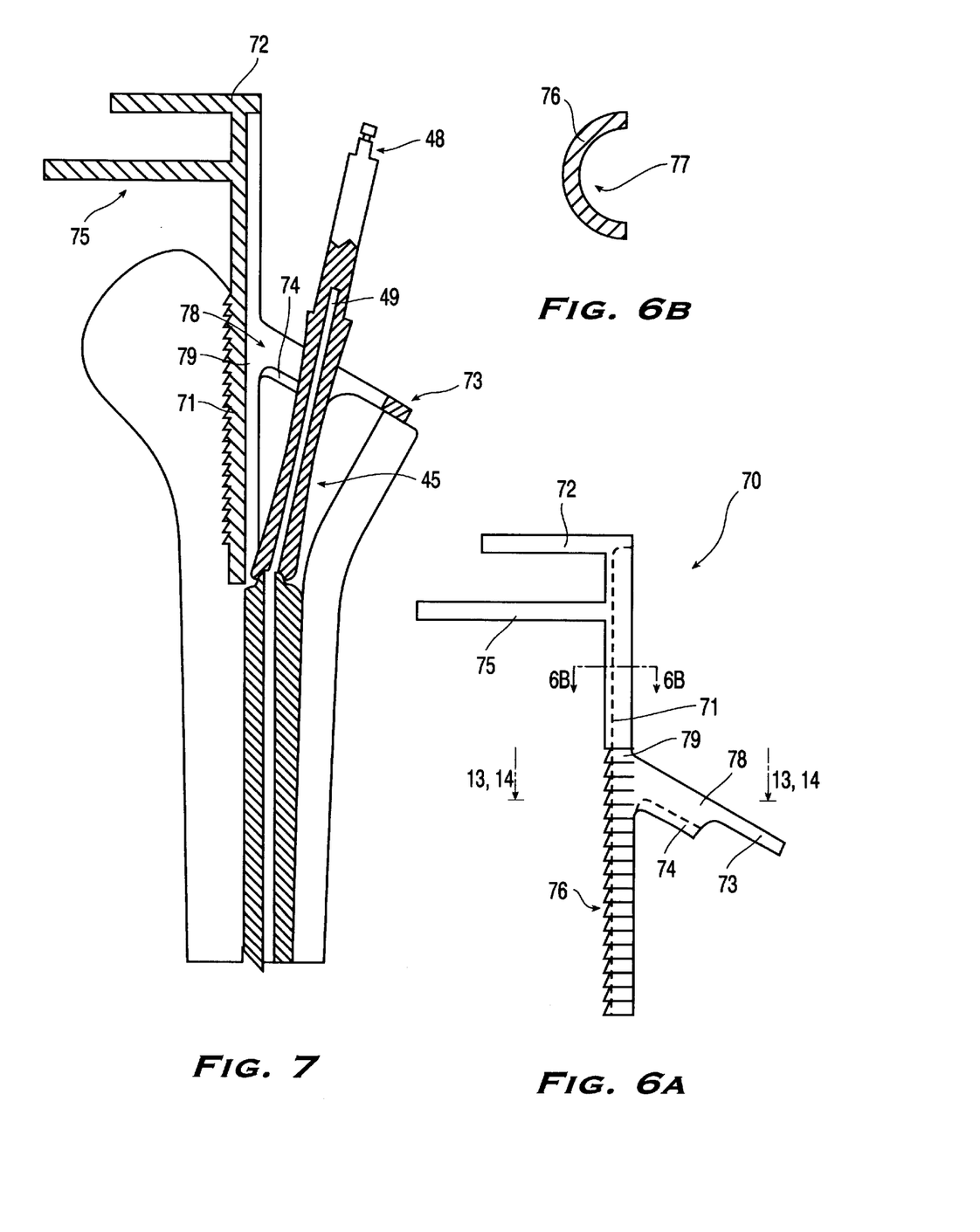
FIG. 6A is an elevational view, in cross-section, of a first embodiment of a metaphyseal template for use with the reaming apparatus of FIGS. 1–4.
FIG. 6B is a plan view, in cross section, of the elongated member of the metaphyseal template along line A—A of FIG. 6A.
FIG. 7 is an elevational view, in cross-section, of the metaphyseal template of FIGS. 6A and 6B in use with the reaming apparatus of FIG. 4.

In a third embodiment of the invention, shown FIGS. 6A through 7, there is provided a metaphyseal template 70, corresponding to a hollow version of the prosthesis, to guide the proximal reamer in shaping the remaining bone to match the medial and anterior-posterior curves of the prosthesis, for use with the reamers 44 or 63, shown in FIGS. 2 and 5, respectively, in forming the calcar region 62 of the femur. The metaphyseal template 70, as shown in FIGS. 6A and 6B, comprises an elongated member 76, comprising a partially circular cavity 77 the rear wall of which partially comprises cutting teeth 71, an elliptical hollow member 73, radiating medially from the side edges, and at an angle relative to the longitudinal axis, of the elongated member, the rear wall of which comprises a portion of the wall of the elongated member 76, two protrusions 78, extending distally from said ring at the rear ends thereof, terminating in knife edges 74; impact receiving means 72 extending laterally at the top edge of elongated member 76 and normal thereto and anteversion control means 75 extending laterally from, and normally to the longitudinal axis of, the elongated member 76.

The elongated member 76 comprises a half-cylinder (open) whose radius of curvature corresponds to the radius of the lateral bore 52. The elliptical hollow member 73 is shaped as the most proximal edge of the prosthesis. The anterior portion of hollow member 73 comprises a portion of elongated member 76 the angle between hollow member 73 and the elongated member 76 corresponding to the angle between the proximal surface of the prosthesis and the longitudinal axis of the lateral bore 52. Two protrusions 78, to aid in seating the template in the bone, extend distally from the lower surfaces of the posterior and anterior lateral portions of hollow member 73. The protrusions 78 terminate in knife edges 74. The impact receiving means 72 facilitates setting of the template in the osteotomy cut.

Figure 13:
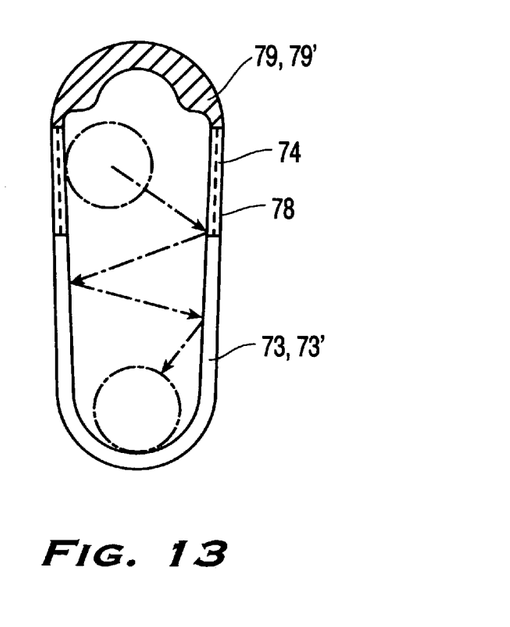
FIG. 13 is a plan view of the hollow member of the metaphyseal templates of FIGS. 6A, 6B, 9A and 9B showing one mode of reamer movement within the template.
Figure 14:
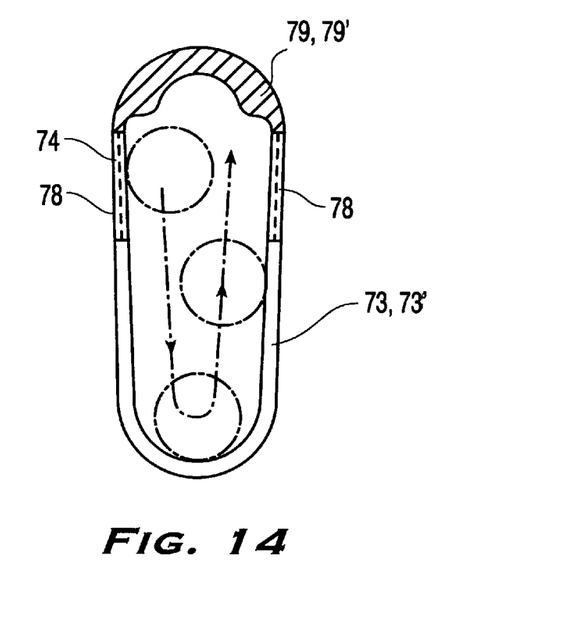
FIG. 14 is a plan view of the hollow member of the metaphyseal templates of FIGS. 6A, 6B, 9A and 9B showing a second mode of reamer movement within the template.

In the practice of this embodiment of the invention the distal canal is reamed to cortical using the reaming system of the first embodiment except for the curved reamer 44 of FIG. 2. The elongated member 76, of template 70, is introduced axially into the lateral bore 52, anteversion is set by means of anteversion control 75 end hollow member 73 seated, by tapping an the impact receiving means 72, into the osteotomy cut. The alignment of the lateral bore 52 and osteotomy cut are checked and, if necessary, manipulated by setting the anteversion and rotating the axis to move the outline of the prosthesis into the proper version. A reamer 45, whose greatest outer diameter is less than the inner diameter of the lateral medullary bore 52, but, in all other respects corresponding to reamer 44, is inserted into the lateral bore 52 through the opening in the hollow member 73. The calcar region 62 of the bone is then shaped by manipulating reamer 45 in a medial direction in the hollow portion of the ring 73, corresponding to the proximal surface of the implant, by a series of motions, posterior-anterior as shown in FIG. 13 or lateral-medial as shown in FIG 14. The template and reamers are then removed and the prosthesis set into the osteotomy.

Figures 8, 9A, 9B:
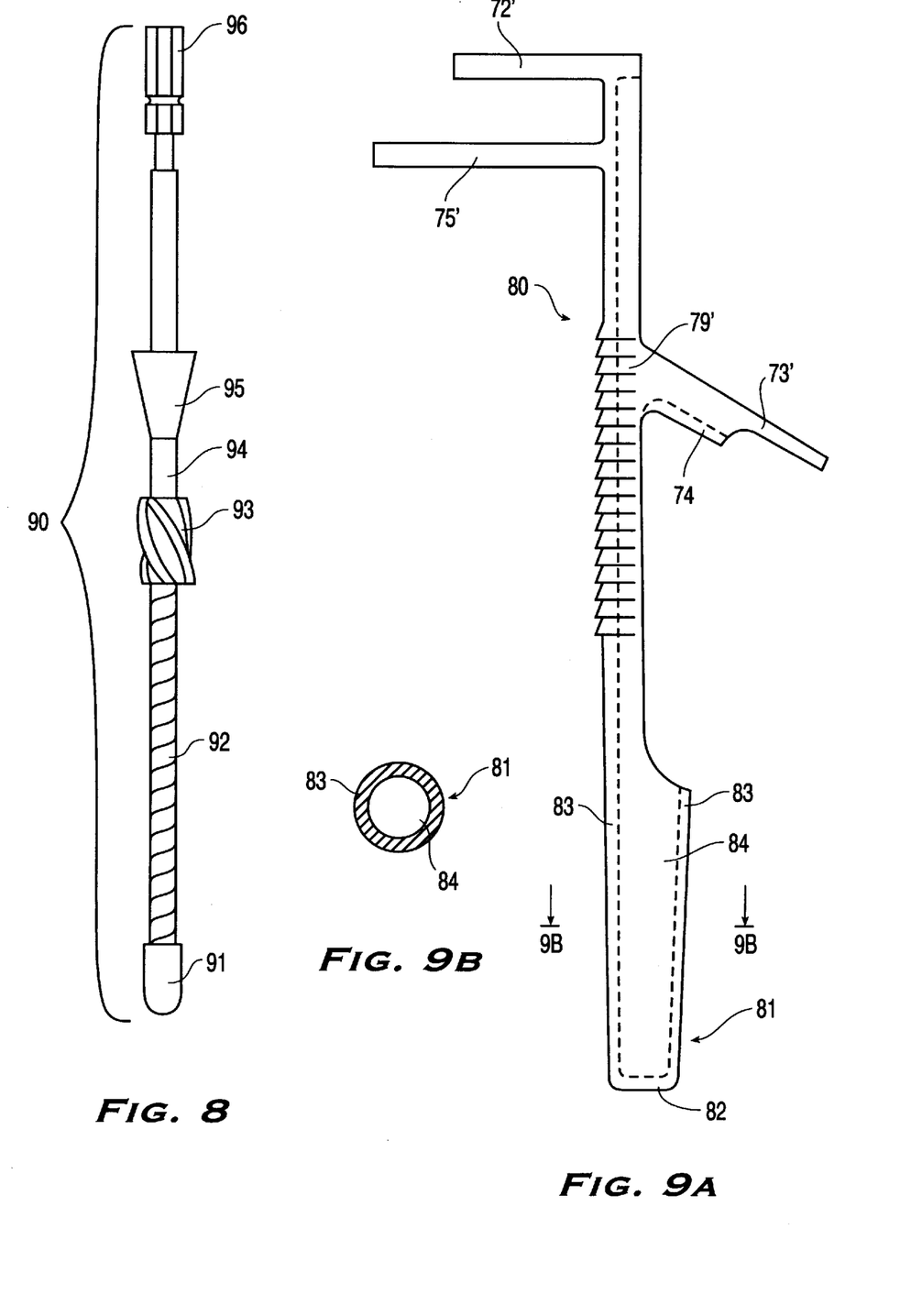
FIG. 8 is an elevational view, in cross-section, of a modification of the reaming apparatus of FIG. 5.
FIG. 9A is an elevational view, in cross-section, of a second embodiment of the metaphyseal template for use with the reaming apparatus of FIGS. 5 and 8.
FIG. 9B is a plan view, in section of the elongated member of the metaphyseal template along line B—B of FIG. 9A.
Figure 10:
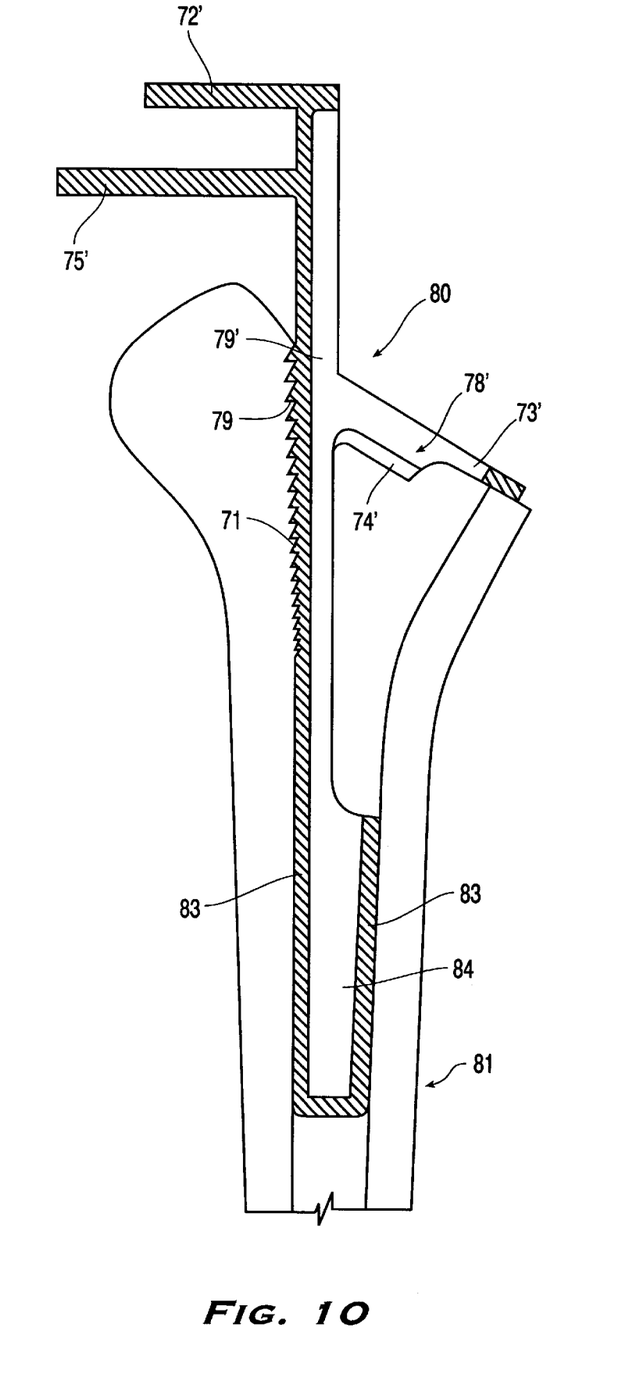
FIG. 10 is an elevational view, in cross-section, of the metaphyseal template of FIGS. 9A and 9B inserted into the lateral lateral bore of a long bone.
Figure 11:
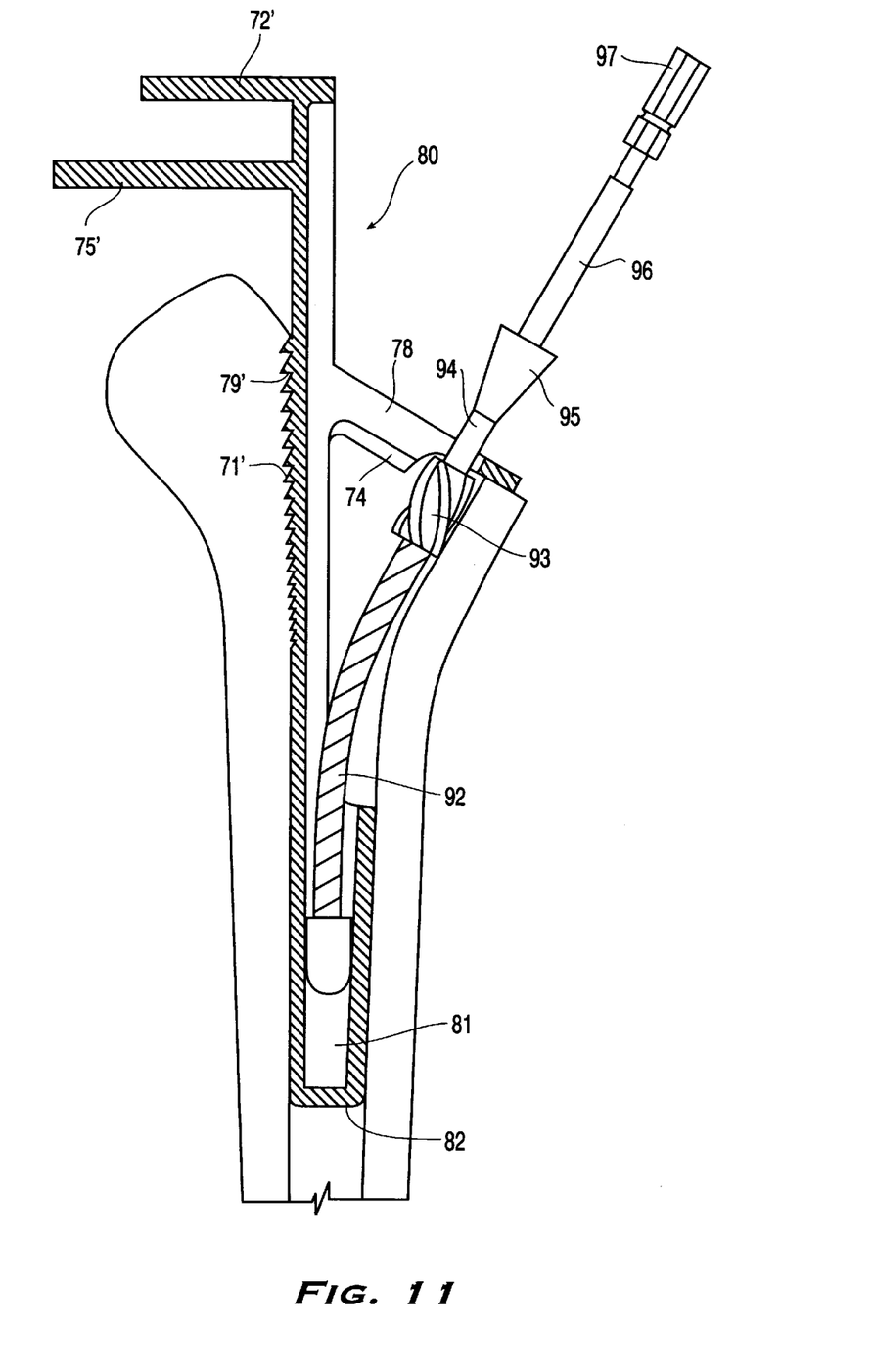
FIG. 11 is an elevational view, in cross-section, of a modification of FIG. 10 wherein the reaming apparatus has been inserted into the metaphyseal template after removal of proximal portion of the calcar region.
Figure 12:
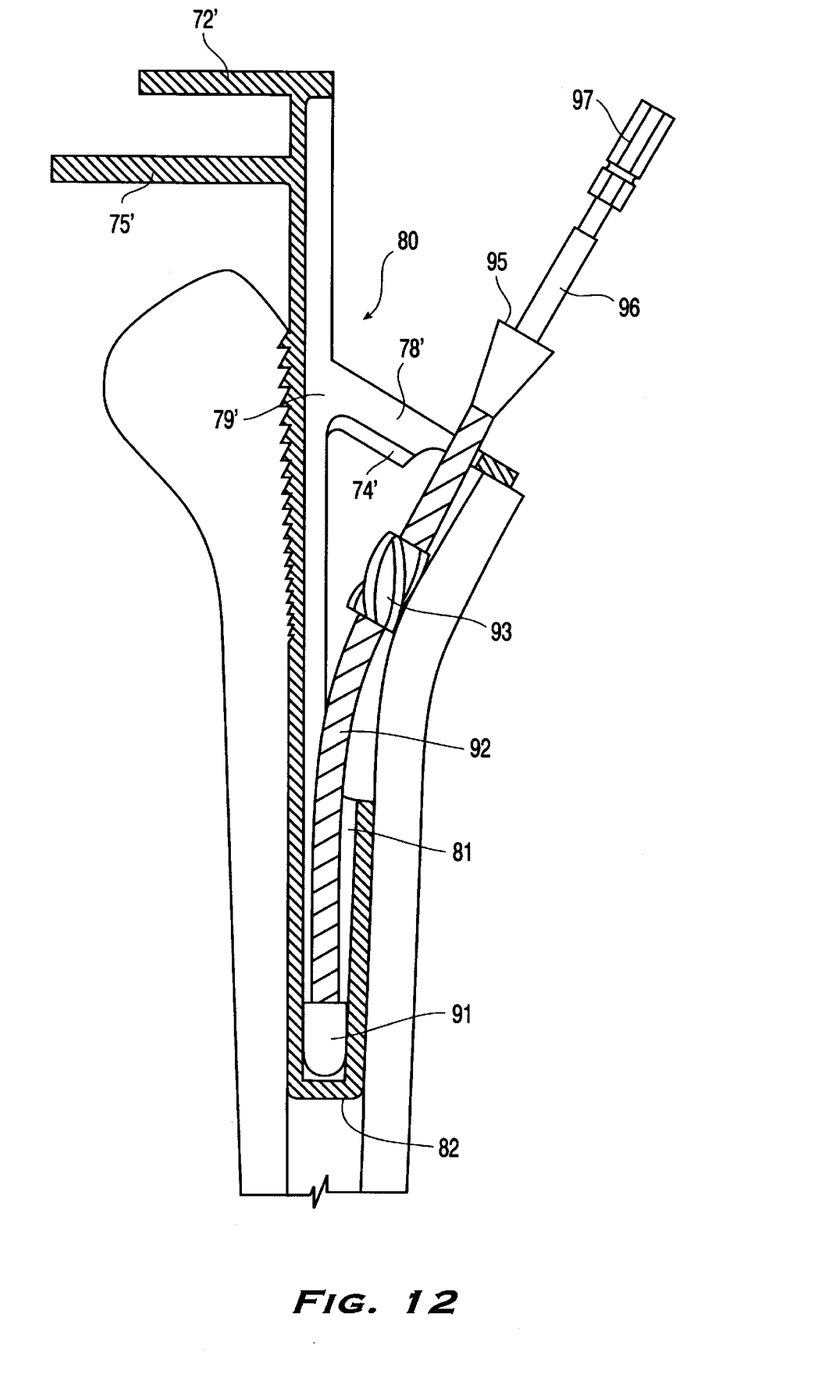
FIG. 12 is an elevational view, in cross-section, similar to FIG. 11 showing the reaming apparatus at a later stage.

A fourth embodiment of the invention, shown in FIGS. 8–12, comprises a template 80 for use with a reamer apparatus such as those shown in FIGS. 5 and 8. Template 80 shown in FIGS. 9A and 9B, comprises template 70, of the above embodiment further comprising a full, cannulated cylinder 81 at the distal end of elongated member 76. In this embodiment the reamer apparatus 90, shown in FIG. 8, comprises a smooth, distal head 91 fixedly attached to the first end of a flexible shaft 92 and a concave reamer 93 fixedly attached to the second end of the shaft 92 and to the first end of a solid shaft 94 which has a connector 96, for connection to a rotary power transmission source (not shown). The reamer apparatus 90 further comprises a fluted portion 95 disposed proximally from the reamer 93 along rigid shaft 94. Fluted portion 95 provides means to guide the reamer apparatus within the hollow member 73 of template 80.

In the practice of this embodiment of the invention the template 80 is set into the osteotomy by means of cutting teeth 71 on the rear surface of the elongated member 76, and knife edges 74 on the hollow member 73. The smooth head 91, of reamer apparatus 90, is passed into cylinder 81 through the lateral bore 52. The calcar region 62 of the bone is then shaped by flexing flexible shaft 92 and manipulating reamer portion 93 in a medial direction in the hollow portions of hollow member 73 (corresponding to the proximal surface of the implant) by a series of motions, such as those shown in FIG. 13 and 14. The template and reamers are then removed and the prosthesis set into the osteotomy. The alignment of the lateral bore 52 and osteotomy cut are checked and, if necessary, manipulated by setting the anteversion and rotating the axis to move the outline of the prosthesis into the proper version.

While several examples of the present invention have been described, it is obvious that many changes and modifications may be made thereunto, without departing from the spirit and scope of the invention.

We claim:

1. An apparatus for reaming a medullary canal in a bone comprising:

a flexible shaft having a distal end a rigid proximal end for engagement with a rotary power transmission source;

a head having a distal end comprising a first reamer and a proximal end coupled to said distal end of said flexible shaft for rotation therewith;

a second reamer having a bore defined therethrough for slideably receiving said flexible shaft, a proximal end, and a distal end;

a drive coupling at least on said head and said second reamer such that at least said second reamer rotates with said first reamer and said flexible shaft; and a third reamer positioned on said flexible shaft to ream the proximal portion of a bone;

wherein:

when said second reamer is slid onto said flexible shaft, said distal end of said second reamer is adjacent said proximal end of said head and coupled directly by said drive coupling; and said flexible shaft is flexed from a straight configuration to position said third reamer to ream in an arc in a proximal portion of a bone.

2. The apparatus of claim 1, wherein:

said third reamer has a bore defined therethrough for slideably receiving said flexible shaft;

said third reamer has a distal end with a cavity shaped to engage said proximal end of said second reamer;

a drive coupling is provided at said distal end of said third reamer and said proximal end of said second reamer; and said first, second and third reamers are coupled together via said drive couplings.

3. The apparatus of claim 2, wherein said second reamer has a generally conically shaped cutting portion tapering radially inwardly from said proximal end thereof to said distal end thereof.

4. The apparatus of claim 2, wherein said drive coupling at said distal end of said third reamer and said proximal end of said second reamer comprises pins and complementary holes mounted on contacting ends of a respective one of said second and third reamers.

5. The apparatus of claim 2, wherein said third reamer has a generally cylindrical cutting shape.

6. The apparatus of claim 1, wherein said flexible shaft has a stop element attached between said head and said second reamer to contact and locate said distal end of said second reamer with respect to the axial length of said flexible shaft.

7. The apparatus of claim 1, wherein said third reamer comprises:

a concave cutting surface;

a distal end having a cavity shaped to receive said rigid proximal end of said flexible shaft; and a proximal end having a drive connection shaft attached thereto, said drive connection shaft having a proximal end comprising a connector shaped to engage a rotary power transmission source.

8. The apparatus of claim 7, further comprising a template shaped to guide said third reamer in removing bone material from the calcar region of the long bone having a lateral elongated bore therein, said template comprising:

an elongated member comprising a partially circular cavity having side edges and a rear wall partially comprising cutting teeth;

an elliptical hollow member radiating from said side edges at an angle relative to the longitudinal axis of said elongated member, said hollow member having a rear wall comprising a portion of said rear wall of said elongated member;

two protrusions extending distally from said hollow member and terminating in knife edges;

impact receiving means extending laterally at the top edge of said elongated member and normal thereto; and anteversion control means extending laterally from, and normally to the longitudinal axis of, said elongated member.

9. The apparatus of claim 7, wherein:

said third reamer is driven independently of said first and second reamers; and said cavity in said distal end of said third reamer is shaped to permit universal movement between said second and third reamers.

10. An apparatus for reaming the medial portion of a medullary canal in the calcar region of a long bone having a lateral bore, said reaming apparatus comprising:

a flexible shaft having distal and proximal ends;

a first element attached to said distal end of said flexible shaft and having an outer diameter about equal to the inner diameter of the lateral bore of the bone;

a reamer having a distal end coupled to said proximal end of said flexible shaft, a proximal end, and a concave cutting surface for reaming a convex shape in the calcar portion of the bone; and a solid shaft having a distal end attached to said proximal end of said reamer and a proximal end; and a connector at said proximal end of said solid shaft shaped for engagement with a rotary power transmission source.

11. The apparatus of claim 10, wherein said first element comprises a smooth surface.

12. The apparatus of claim 10, wherein said first element comprises a cutting surface.

13. The apparatus of claim 10, further comprising a template shaped to guide said reamer in removing bone material from the calcar region of the long bone having a lateral elongated bore therein, said template comprising:

an elongated member comprising a partially circular cavity having side edges and a rear wall partially comprising cutting teeth;

an elliptical hollow member radiating from said side edges at an angle relative to the longitudinal axis of said elongated member said hollow member having a rear wall comprising a portion of said rear wall of said elongated member;

two protrusions extending distally from said hollow member and terminating in knife edges;

impact receiving means extending laterally at the top edge of said elongated member and normal thereto; and anteversion control means extending laterally from, and normally to the longitudinal axis of, said elongated member.

14. The apparatus of claim 10, further comprising a metaphyseal template comprising:

an elongated member having a rear wall, side edges, and a distal end with a full, cannulated cylinder; and an elliptical hollow member radiating from said side edges at an angle relative to the longitudinal axis of said elongated member, said hollow member having a rear wall comprising a portion of said rear wall of said elongated member;

wherein the outer diameter of said cannulated cylinder is about equal to the inner diameter of the lateral bore of the bone at the isthmus and the outer diameter of element of said reaming apparatus is about equal to the inner diameter of said cannulated cylinder.

15. An apparatus for reaming the medial portion medullary canal in the calcar region of a long bone, containing a lateral bore, said reaming apparatus comprising:

a metaphyseal template having an elongated member with a distal end, a cannulated cylinder at said distal end of said elongated member, and a hollow member radiating from said elongated member;

a flexible shaft having a distal end and a proximal end;

a first element attached to said distal end of said flexible shaft and having an outer diameter equal to the inner diameter of said cannulated cylinder of said template;

a reamer having a proximal end, a distal end fixedly attached to said proximal end of said flexible shaft, and a cylindrical cutting surface for reaming a convex shape in the calcar portion of the bone; and a rigid shaft having a distal end fixedly attached to said proximal end of said reamer and a proximal end having a connector shaped for engagement of said rigid shaft with a rotary power transmission source; and a fluted portion attached to and spaced between said distal and proximal ends of said rigid shaft to guide said flexible shaft within said hollow portion of said template.

16. A method of preparing a long bone, comprising an opening in the trochanteric fossa, to receive a prosthesis, said method comprising the steps of:

initially forming a lateral bore by means of a reaming apparatus having at least a proximal reamer and a distal reamer coupled to a flexible shaft; and then reaming the calcar portion of the bone to complete the shape of the prosthesis by flexing said flexible shaft of said reaming apparatus to position said proximal reamer against the calcar position.

17. The method of claim 16, wherein said bone comprises a bore to receive a guide wire and said reaming apparatus is cannulated to pass the guide wire therethrough.

18. The method of claim 16, wherein:

said proximal reamer is replaced by a third reamer having a proximal end with a connector coupled thereto, a distal end with a cavity defined therein, and a concave cutting surface;

said proximal portion of said flexible shaft has a connector inserted into said cavity of of said third reamer;

said connector on said third reamer is coupled with the rotary power transmission source; and said proximal end of said flexible shaft is flexed and the calcar bone area reamed by said third reamer to complete the shape of the prosthesis.

19. The method of claim 16, further comprising the steps of:

removing said reaming apparatus;

inserting the head of a second reaming apparatus having a reamer with a concave cutting surface with a distal edge into the bore until the distal edge of said cutting surface of said reamer reaches the proximal portion of the calcar region;

removing the calcar bone in a lateral-medial direction until the cortical bone is reached;

further inserting said head into the bore and removing additional calcar bone until the cortical bone is again reached; and repeating the above process until all of the bone in the calcar region has been removed.

20. The method of claim 18, wherein a metaphyseal template is inserted into the lateral bore of the bone prior to formation of the calcar region and said proximal reamer is replaced by said third reamer.

21. A method of preparing a bone to receive a prosthesis, said method comprising the steps of:

inserting into the lateral bore of the bone a metaphyseal template comprising an elongated member having a partially circular cavity with a rear wall partially comprising cutting teeth, a cannulated cylinder at a distal end of said elongated member, an elliptical hollow member radiating from said elongated member at an angle to the longitudinal axis of the elongated member, impact receiving means extending laterally at the top of said elongated member and normal thereto, and anteversion control means extending laterally from and normal said elongated member;

seating said template at the proximal end of the calcar portion of the bone by means of the impact receiving means and the anteversion control means;

providing a reamer apparatus comprising a first head at a distal end of said reamer apparatus, a flexible shaft, and a reamer at a proximal end of said flexible shaft;

passing said first head of said reamer apparatus through said hollow portion of said template and into said cannulated cylinder; and reaming the calcar region of the bone by flexing said flexible shaft of said reamer apparatus and manipulating said reamer in a medial direction in said hollow portions of said hollow member by a series of motions.

22. An apparatus for reaming a bone canal comprising:

a flexible shaft having a first end shaped for engagement with a rotary power transmission source, and a second end;

a first reamer coupled to said second end of said flexible shaft for rotation therewith;

a second reamer having a bore therethrough for slideably receiving said flexible shaft, said second reamer having a first end which, when said second reamer is slid onto said flexible shaft, is adjacent said first reamer, and a second end; and a third reamer having a bore therethrough for slideably receiving said flexible shaft, said third reamer having a first end for engaging a second end of said second reamer shaped to permit universal movement between said second and third reamers wherein:

said first and second reamers have a drive coupling therebetween such that said first and second reamers are rotated together with said flexible shaft;

said third reamer is driven independently from said first and second reamers; and said flexible shaft is flexed from a straight configuration to position said third reamer to ream in an arc in a proximal portion of a bone.

23. The apparatus of claim 22, wherein said second reamer has a generally conically shaped cutting portion tapering radially inwardly from said second end thereof to said first end thereof.

24. The apparatus of claim 22, wherein said third reamer has a concave cutting surface for cutting a convex shape in bone surrounding the bone canal.

25. The apparatus of claim 22, wherein said flexible shaft has a stop element attached thereto to contact and locate said first end of said second reamer with respect to the axial length of said flexible shaft.

26. The apparatus as set forth in claim 22, wherein said first end of said third reamer and said second end of said second reamer as a ball and socket joint with one of said ball and socket mounted on contacting ends of a respective one of said second and third reamers.

27. The apparatus as set for the in claim 22, wherein said third reamer has a generally cylindrical cutting surface.

28. An apparatus for reaming a femoral medullary canal comprising:

a flexible drive shaft having a proximal end with a solid shaft portion and a distal portion;

a first reamer coupled to said distal portion of said flexible shaft and driven by said flexible shaft;

a second reamer having a concave cutting surface, said second reamer mounted on a proximal portion of said flexible shaft for reaming a convex shape on the proximal portion of said femoral canal; and     means for rotating said first and second reaming elements.

29. The apparatus as set forth in claim 28, further including a third reamer intermediate said first and second reamers, said third reamer having a bore therethrough, a distal end adjacent said first reamer, and a proximal end adjacent said second reamer for reaming a midshaft region of said canal.

30. The apparatus as set forth in claim 28, wherein said second reamer has a bore therein for slideably receiving said flexible shaft.

31. The apparatus as set forth in claim 30, wherein said means for rotating said second reamer is independent of said flexible shaft.

* * * * *

UNITED STATES PATENT AND TRADEMARK OFFICE
CERTIFICATE OF CORRECTION

PATENT NO. : 5,908,423
DATED : June 1, 1999
INVENTOR(S) : Kashuba et al.

It is certified that error appears in the above-identified patent and that said Letters Patent is hereby corrected as shown below:

Column 1, line 21, "remers" should read --reamers--.

Column 1, line 43, "has" should read --have--.

Column 2, line 17, "has" should read --have--.

Column 2, line 23, "now" should read --new--.

Column 2, line 26, after "specially" insert --shaped--.

Column 2, line 29, "late" should read --lateral--.

Column 2, line 31, "able" should read --flexible--.

Column 2, line 34, "bail" should read --ball--.

Column 3, line 57, "he" should read --the--.

Column 4, line 32, "to" should read --the--

Column 4, line 53, "produce" should read --producing--.

Column 5, line 34, delete "lateral" (first occurrence).

Column 6, line 10, "retainer" should read --reamer--.

Column 6, line 21, after "proximal" insert --end--. ; delete "and".

UNITED STATES PATENT AND TRADEMARK OFFICE
CERTIFICATE OF CORRECTION

PATENT NO. : 5,908,423
DATED : June 1, 1999
INVENTOR(S) : Kashuba et al.

It is certified that error appears in the above-identified patent and that said Letters Patent is hereby corrected as shown below:

Column 6, line 29, "ream" should read --reamers--.

Column 6, line 30, "rasped" should read --respect--.

Column 7, line 18, after "fixedly" insert --attached--.

Column 8, line 16, "end" should read --and.

Column 8, line 17, before "seated" insert --is--.

Column 10, line 53, after "member" insert --,--.

Column 11, line 55, delete "of" (first occurrence).

Column 12, line 26, after "normal" insert --from--.

Column 13, line 15, "for the" should read --forth--

Signed and Sealed this

Twenty-first Day of December, 1999

Attest:

Q. TODD DICKINSON

*Attesting Officer*  *Acting Commissioner of Patents and Trademarks*